United States Patent [19]

Treaftis et al.

[11] 3,949,594
[45] Apr. 13, 1976

[54] TWO-STAGE DISPOSABLE PARTICLE SAMPLING HEAD

[75] Inventors: Harry N. Treaftis; Thomas F. Tomb, both of Pittsburgh, Pa.

[73] Assignee: The United States of America as represented by the Secretary of Interior, Washington, D.C.

[22] Filed: Sept. 25, 1974

[21] Appl. No.: 509,153

[52] U.S. Cl. ................................. 73/28; 55/270
[51] Int. Cl.² ................................. G01N 15/06
[58] Field of Search .............. 73/28, 432 PS; 55/270

[56] References Cited
UNITED STATES PATENTS

| | | | |
|---|---|---|---|
| 2,894,877 | 7/1959 | Sinden | 73/28 X |
| 3,001,914 | 9/1961 | Andersen | 73/28 |
| 3,092,583 | 6/1963 | Wolff et al. | 73/28 X |
| 3,686,835 | 8/1972 | Strange et al. | 73/28 X |
| 3,693,457 | 9/1972 | Pilat | 73/28 X |
| 3,795,135 | 3/1974 | Andersen | 73/28 |

*Primary Examiner*—Richard C. Queisser
*Assistant Examiner*—Stephen A. Kreitman
*Attorney, Agent, or Firm*—Gersten Sadowsky; Donald R. Fraser

[57] ABSTRACT

An integral, two-stage aerosol sampling head for collecting and separating airborne particulate contaminants into two size fractions is provided which comprises a moulded housing containing an impaction plate as a first stage for removing and collecting particles having an aerodynamic equivalent diameter (AED) greater than $10\mu m$ in size and a filter as a second stage for removing and collecting particles having an AED less than $10\mu m$ in size. The sampling head assembly of the invention eliminates the separate first-stage cyclone separator of conventional personal aerosol sampling assemblies used by coal mine operators and inspectors to monitor the quality of air in coal mines.

2 Claims, 3 Drawing Figures

TWO-STAGE DISPOSABLE PARTICLE SAMPLING HEAD

FIELD OF THE INVENTION

The invention relates to devices for collection and classification of particulate contaminants suspended in air, and, more particularly, to a disposable contaminant sampling head particularly adapted for collecting and separating airborne particulate contaminants in mine areas into two size fractions.

BACKGROUND OF THE INVENTION

The 1969 Federal Coal Mine Health and Safety Act requires "each operator of a coal mine to take accurate samples of the amount of respirable dust in the mine atmosphere to which each miner in the active working place of such mine is exposed." The amount of respirable dust referred to in the Act is "the average concentration of respirable dust if measured with an MRE instrument or such equivalent concentrations if measured with another device approved by the Secretary and the Secretary of Health, Education, and Welfare." Part 74 of Title 30, Code of Federal Regulations, sets forth the requirements which must be met in order to be an approved alternate sampling device.

At the present time there are several personal respirable dust samplers, i.e., samplers which can be carried by the miners, which have been approved as alternate devices for sampling coal mine environments. Each approved device consists of a pump unit, a sampling head assembly, and, if rechargeable batteries are used in the pump unit, a battery charger.

The sampling head assembly, the construction of which is essentially the same for all of the approved alternate units, consists of a 10 mm cyclone separator, and a compatible filter assembly. The function of the cyclone separator is to separate the non-respirable fraction of the particulate contaminants in the sampled aerosol from the respirable fraction. The respirable dust, i.e., that fraction which penetrates through the cyclone, is collected by the filter assembly.

Although the present cyclone-filter configuration of the sampling head assembly has been accepted and is in widespread use throughout the coal mining industry, it suffers several disadvantages. At a mass respirable dust concentration of 2.0 milligrams per cubic meter of air, which is the mandatory maximum standard for underground and surface coal mines, the total sample mass collected during a full working shift is often less than one milligram. The analytical precision error for a mass of this magnitude can be as high as twenty percent. Further, the cyclone separator requires daily cleaning and maintenance. Proper assembly and alignment of the cyclone and filter stages requires several o-ring seals between assembly stages to prevent air leaks. Faulty o-rings are difficult to detect and can result in excessive sampling error.

SUMMARY OF THE INVENTION

According to the invention, an integral, two-stage sampling head is provided which comprises a housing containing an impaction plate as a first stage for removing and collecting the particulate contaminant having an AED greater than 10 $\mu$m in size from the sampled aerosol, and a second-stage filter for removing and collecting the particulate contaminants having an AED less than 10 $\mu$m in size from the sampled aerosol. This arrangement advantageously eliminates the need for the separate cyclone separator and hence eliminates the maintenance and assembly problems associated with such separators. In addition the sampling head of the invention reduces analytical precision error by collecting approximately a fifty percent larger mass sample and is capable of being manufactured on a low cost mass production basis so that after use, the sampling head can be discarded. These advantages are accomplished by maintaining the performance criteria required for acceptance as an alternative sample assembly.

Other features and advantages of the invention will be set forth in, or will be apparent from, the detailed description of the preferred embodiments found herein below.

DESCRIPTION OF THE PREFERRED EMBODIMENTS

Figure 1:
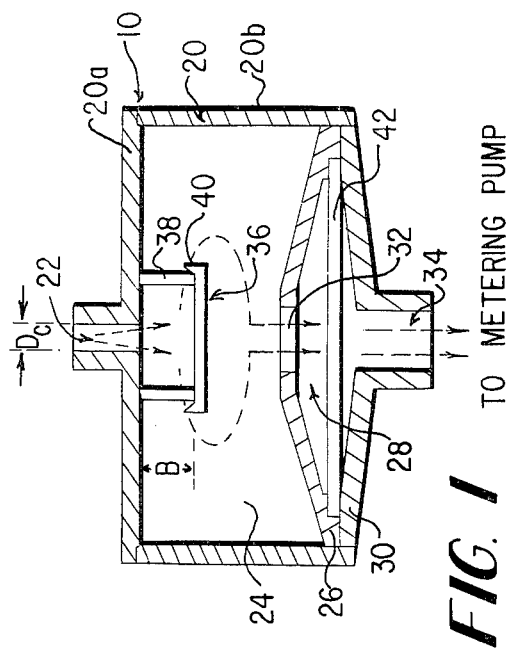
FIG. 1 is a diagrammatic sectional view of a sampling head according to the invention.
Figure 2:
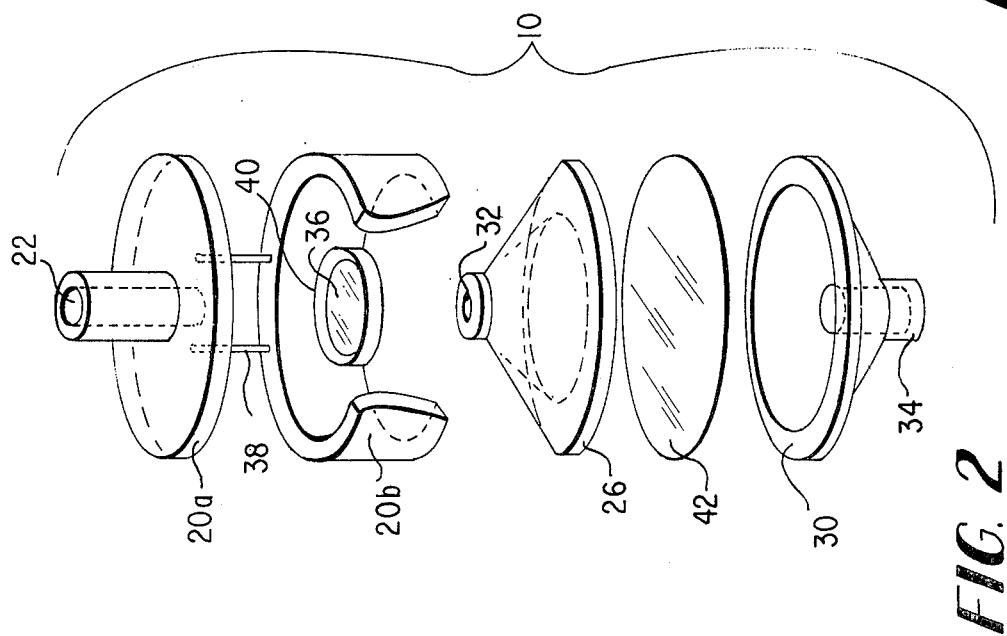
FIG. 2 is an exploded perspective view, partially in section, of the sampler of FIG. 1.

Referring to FIGS. 1 and 2, a two-stage sampling head denoted 10, comprises a generally cylindrical housing 20 with an aerosol inlet 22. As illustrated, the housing 20 can be of two-part construction including a cover 20a and a cylindrical base 20b, although the housing 20 can also be of unitary construction. A particle transfer chamber 24 is formed within housing 20 by the top surface, 26, of the filter holder 26. A secondary particle chamber 28 is formed between upper filter holder 26 and the top of the filter 42. Filter holders 26 and 30 are generally conical in shape and include respective aerosol outlets 32 and 34 therein as illustrated.

Figure 3:
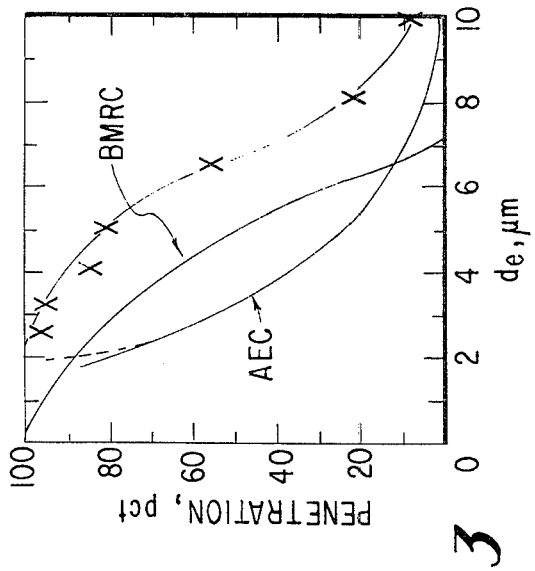
FIG. 3 is a graph which compares the percent penetration of particles through the first stage of a sampling assembly of the invention versus particle diameter, with recommended respirable mass criteria as set by the United States Atomic Energy Commission and British Medical Research Council.

Within the particle chamber 24, and disposed a distance B below inlet 22, is particle impaction plate 36. Impaction plate 36, which is suspended from cover 20a by dependent struts 38, serves as the first-stage for separating contaminant particles, i.e. having an AED greater than 10 $\mu$m in size, from the sampled aerosol. Plate 36 can, as illustrated, be provided with a lip 40 to retard particle re-entrainment, although a flat plate can also be used. Plate 36 may also be provided with a coating (not shown) of a suitable adhesive, e.g., high vacuum grease, to aid retention of impacted particles. The ratio of the distance of the first stage impaction plate 36 from the inlet, B, to the diameter of the inlet 22, $D_c$, i.e., the ratio $B/D_c$, should be about 0.75 to obtain the calibration curve, FIG. 3.

A conventional, 37 mm diameter, 5 $\mu$m pore size, respirable particle filter 42 is held by filter holders 26 and 30 within chamber 28. Filter 42 serves as the second-stage of the sampler 10, removing and collecting the contaminant particles having an AED less than 10 $\mu$m in size from the sampled aerosol.

Thus, when a metering pump (not shown) is attached to outlet 34, air, containing suspended contaminants, e.g., coal mine dust, in the vicinity of a person wearing the sampling head assembly, is drawn into aerosol inlet 22. The air, denoted by dotted arrows in FIG. 1, impinges upon plate 36 and is caused to re-direct at right angles from its entrance direction. The larger particles with AED greater than 10 μm because of their inertia, impact onto plate 36. The aerosol stream, with the large particles removed, passes through chamber 24 into chamber 28, and thence through filter 42 where the smaller particles with AED less than 10 μm are removed and collected for subsequent measurement.

It will be appreciated from the foregoing that the sampling head of the invention is simple and can be easily and inexpensively manufactured. Further, the sampling head of the invention eliminates the need for the cyclone separator of conventional assemblies, and hence the maintenance and assembly problems attendant such assemblies. As shown in FIG. 3, the penetration characteristics of the first stage of the invention are greater than the penetration characteristics of the respirable mass criteria adopted by the United States Atomic Energy Commission (AEC) and the British Medical Research Council (BMRC). This greater penetration through the first stage of the sampling head assembly of the invention allows approximately a 50 percent larger mass sample to be collected on the filter over conventional cyclone-filter assemblies, thus reducing the analytical precision error.

Although the invention has been described relative to specific embodiments of the invention, it will be appreciated by one skilled in the art that modifications and variations in these embodiments can be effected without departing from the spirit and scope of the invention.

We claim:

1. An integral, two stage, disposable personal dust sampling head whereof a housing contains a first stage chamber arranged contiguous to a second stage chamber, and is adapted to have an aerosol sample of dust drawn therethrough between inlet and outlet ends thereof, and wherein said housing comprises an overall enclosure having as integral parts thereof at said inlet and outlet ends of said housing a first cover element including an aerosol inlet means and a second cover element including an aerosol outlet means, respectively, a particle filter is operatively maintained by a filter holder element having a central opening therein, said filter holder element being affixed within said housing in peripheral contact with said second cover element to constitute said second chamber therebetween in which said particle filter is situated between said outlet means and said central opening so as to partition said second chamber, an integrally formed, impermeable collector impaction plate is operatively maintained by suspension from said first cover element such that said filter holder element, said enclosure and said first cover element constitute said second chamber about said impaction plate spatially positioned therein between said inlet means and said central opening, and upon operation of a pumping means connected to said outlet means said aerosol sample is received in said first and second chambers where non-respirable contaminant particles suspended in said aerosol sample which have an aerodynamic equivalent diameter of greater than 10 μm in size are removed and collected by said impaction plate, and respirable contaminant particles suspended in said aerosol sample which have an aerodynamic equivalent diameter of less than 10 μm in size are removed and collected by said particle filter, respectively.

2. A sampling head as set forth in claim 1 wherein said impaction plate is provided with a lip around a periphery thereof for retarding re-entrainment of particles removed from said aerosol.

* * * * *